(12) United States Patent
Vanden Berghe et al.

(10) Patent No.: US 11,291,423 B2
(45) Date of Patent: Apr. 5, 2022

(54) SYSTEM AND METHOD OF RADIOGRAPH CORRECTION AND VISUALIZATION

(71) Applicant: MATERIALISE N.V., Leuven (BE)

(72) Inventors: Peter Vanden Berghe, Leuven (BE);
Christophe Van Dijck, Leuven (BE);
Barbara Friedberger, Leuven (BE);
Roel Wirix-Speetjens, Leuven (BE);
Ward Bartels, Leuven (BE)

(73) Assignee: Materialise N.V., Leuven (BE)

( * ) Notice: Subject to any disclaimer, the term of this patent is extended or adjusted under 35 U.S.C. 154(b) by 0 days.

(21) Appl. No.: 16/630,840

(22) PCT Filed: Jul. 13, 2018

(86) PCT No.: PCT/US2018/042073
§ 371 (c)(1),
(2) Date: Jan. 13, 2020

(87) PCT Pub. No.: WO2019/014585
PCT Pub. Date: Jan. 17, 2019

(65) Prior Publication Data
US 2020/0138394 A1 May 7, 2020

Related U.S. Application Data

(60) Provisional application No. 62/666,962, filed on May 4, 2018, provisional application No. 62/664,865, filed
(Continued)

(51) Int. Cl.
*A61B 6/00* (2006.01)
*G06T 11/00* (2006.01)
(Continued)

(52) U.S. Cl.
CPC ............ *A61B 6/5211* (2013.01); *A61B 6/022* (2013.01); *A61B 6/463* (2013.01); *G06T 11/008* (2013.01);
(Continued)

(58) Field of Classification Search
CPC ......... G06T 19/00; G06T 17/20; G06T 17/00; G06T 15/10; G06T 15/00; A61B 6/5211;
(Continued)

(56) References Cited

U.S. PATENT DOCUMENTS

2003/0073901 A1* 4/2003 Simon .................... A61B 34/20
600/424
2012/0035462 A1* 2/2012 Maurer, Jr. .......... A61N 5/1077
600/411
(Continued)

FOREIGN PATENT DOCUMENTS

EP 3279865 A1 2/2018
IN WO-2016116946 A2 * 7/2016 ........... G06T 7/0012
(Continued)

OTHER PUBLICATIONS

Ayache, Nicholas et al., Medical Image Computing and Computer-Assisted Intervention—MICCAI 2007, 10th International Conference, Oct. 29-Nov. 2, 2007, 12 pages, Brisbane, Australia.
(Continued)

*Primary Examiner* — Todd Buttram
(74) *Attorney, Agent, or Firm* — Patterson + Sheridan, LLP

(57) ABSTRACT

Systems and methods of radiograph correction and visualization are disclosed. Certain embodiments provide a method for generating a 3D model of at least part of one anatomical object based on one or more radiographs. The method further includes positioning the 3D model based on information indicative of a normalized projection compris-
(Continued)

ing information indicative of a desired position and orientation of the at least part of one anatomical object with respect to the projection plane. The method further includes generating a 2D projection of the 3D model onto the projection plane. The method further includes generating one or more modified radiographs of the at least part of one anatomical object based on the 2D projection.

21 Claims, 17 Drawing Sheets

Related U.S. Application Data on Apr. 30, 2018, provisional application No. 62/532,794, filed on Jul. 14, 2017.

(51) Int. Cl.
  *G06T 17/00* (2006.01)
  *A61B 6/02* (2006.01)
  *A61B 90/00* (2016.01)

(52) U.S. Cl.
  CPC .............. *G06T 17/00* (2013.01); *A61B 6/505* (2013.01); *A61B 2090/367* (2016.02); *G06T 2210/41* (2013.01)

(58) Field of Classification Search
  CPC .. A61B 2017/0092; A61B 6/484; A61B 6/485
  See application file for complete search history.

(56) References Cited

U.S. PATENT DOCUMENTS

| | | | |
|---|---|---|---|
| 2014/0129200 A1 | 5/2014 | Bronstein et al. | |
| 2016/0091439 A1* | 3/2016 | O'Hare | G01B 15/00 378/4 |
| 2019/0090962 A1* | 3/2019 | Boettner | A61B 34/20 |

FOREIGN PATENT DOCUMENTS

| | | |
|---|---|---|
| WO | 0064367 A1 | 11/2000 |
| WO | 2011098895 A2 | 8/2011 |

OTHER PUBLICATIONS

Baruchel, Jose et al., X-Ray Tomography in Material Science, Hermes Science Publications, Paris, 2000.

Cotin, Stephane et al., ICTS, an Interventional Cardiology Training System, Center for Innovative Minimally Invasive Therapy, 7 pages, www.cimit.org.

Cotin, Stephane, Computer Based Interactive Medical Simulation, Modeling and Simulation, Universite des Sciences et Technologie de Lille—Lille I, 2008.

Dawson, Steven L. et al., Designing a Computer-Based Simulator for Interventional Cardiology Training, Catheterization and Cardiovascular Interventions, 2000, 51: 522-527.

Duvachelle, Philippe et al., A computer code to simulate X-ray imaging techniques, Nuclear Instruments and Methods in Physics Research, B170, 2000, pp. 245-258.

Ehlke, Moritz et al., Fast Generation of Virtual X-ray Images, for Reconstruction of 3D Anatomy, IEEE Computer Society, 2013, 10 pages.

Freud, Nicolas et al., Simulation of X-Ray NDT Imaging Techniques, Roma 2000 15th WCNDT, France, 6 pages.

Freud, Nicolas et al., Fast and robust ray casting algorithms for virtual X-ray imaging, Nuclear Instruments and Methods in Physics Research, 2006, B248, pp. 175-180.

Gallio, Elena et al., A GPU Simulation Tool for Training and Optimisation in 2D Digital X-Ray Imaging, PLOS One, Nov. 6, 2015, 17 pages.

Inanc, F. et al., Human body radiography simulations: development of a virtual radiography environment, Center for Nondestructive Evaluation, Jul. 24, 1998, 11 pages.

Maier, Andreas et al.. Fast Simulation of X-ray Projections of Spline-based Surfaces using an Append Buffer, Phys Med Biol., Oct. 7, 2013, 25 pages.

Moore, C.S. et al., A method to produce and validate a digitally reconstructed radiograph-based computer simulation for optimisation of chest radiographs acquired with a computed radiography imaging system, The British Journal of Radiology, vol. 84, 2011, pp. 890-902.

Muniyandi, Manivannan et al., Real-time PC based X-ray simulation for interventional radiology training, Studies in health technology and informatics, Feb. 2003, 8 pages.

Sprawls, Jr., Perry, Physical Principals of Medical Imaging, 2nd Edition, 1993.

Vidal, F.P. et al., Simulation of X-ray Attenuation on the GPU, Proceeding of TCPG '09—Theory and Practice of Computer Graphics, 2009, pp. 25-32.

Vidal, F.P. et al., Development and Validation of Real-time Simulation of X-ray Imaging with Respiratory Motion, Computerized Medical Imaging and Graphics, Apr. 2016, pp. 1-15, vol. 49.

Villard, P.F. et al., Simulation of Percutaneous Transhepatic Cholangiography Training Simulator with Real-time Breathing Motion, International Journal of Computer Assisted Radiology and Surgery, Nov. 2009, pp. 571-578, vol. 4.

Van Walsum, Theo et al., CT-based Simulation of Fluoroscopy and DSA for Endovascular Surgery Training, 1997, pp. 273-282.

* cited by examiner

SYSTEM AND METHOD OF RADIOGRAPH CORRECTION AND VISUALIZATION

CROSS-REFERENCE TO RELATED APPLICATIONS

This application claims the benefit of U.S. Provisional Patent No. 62/666,962, filed May 4, 2018, U.S. Provisional Patent No. 62/664,865, filed Apr. 30, 2018, and U.S. Provisional Patent No. 62/532,794, filed Jul. 14, 2017. The content of each of the provisional applications is hereby incorporated by reference in their entirety.

BACKGROUND OF THE INVENTION

Field of the Invention

This application relates to medical imaging. In some aspects, this application relates specifically to systems and methods for radiograph correction and visualization.

Description of the Related Technology

Radiographs are images created using radiography, which is an imaging technique using X-rays to view the internal form of an object. For example, an imaging device includes a source device that generates X-rays that are projected toward an anatomical object (e.g., a bone in a patient). Some amount of the X-rays is absorbed by the anatomical object and the remaining portion of the X-rays is captured by a detector of the imaging device placed behind the anatomical object relative to the source device. The resulting radiograph is a two-dimensional (2D) image. In some cases, the radiograph has gray values (e.g., of pixels that form the 2D image) indicative of the absorption amount of the various X-rays, and accordingly indicative of the density and structural composition of the anatomical object. In some cases, the radiograph has color values (e.g., of pixels that form the 2D image) indicative of the absorption amount of the various X-rays, and accordingly indicative of the density and structural composition of the anatomical object. The radiograph, in some cases, may have other values.

The use of radiographs to plan surgery, such as orthopedic surgery, is common. Typically, planning of such surgery of an anatomical object includes formulating a diagnosis of the condition of an anatomical object, taking measurements of the anatomical object and/or areas surrounding the anatomical object, planning osteotomies of the anatomical object and/or areas surrounding the anatomical object, 2D templating (e.g., choosing an implant type, position, orientation, and/or size based on an overlay of a 2D outline of the implant onto a radiograph of the anatomical object), etc. Similarly radiographs or fluoroscopy images are used to perform intra-operative and post-operative verification or measurements of the anatomical object and/or areas surrounding the anatomical object.

One common problem is that a radiograph only contains a 2D projection of the anatomy (e.g., of the anatomical object), and that many kinds of planning activities assume a particular view of the anatomy (e.g. anteroposterior (AP), lateral, etc.). If the anatomy cannot be properly positioned with respect to the imaging device used to take the radiograph (e.g., a patient is in pain or less mobile), it may not be possible to obtain a radiograph in the particular view desired. The particular view can refer to a position of the anatomy with respect to the imaging machine (e.g., source device and/or detector), and/or to the position and orientation of individual anatomical objects of the anatomy with respect to each other (e.g. the internal/external rotation, flexion/extension and/or abduction/adduction of a joint). If the radiograph's 2D projection does not fully correspond to the particular view of the anatomy, it could lead to measurement errors or incorrect 2D templating (e.g., as discussed in Lechler, Philipp; Frink, Michael; Gulati, Aashish; Murray, David; Renkawitz, Tobias; Bucking, Benjamin; Ruchholtz, Steffen; Boese, Christoph Kolja, "The influence of hip rotation on femoral offset in plain radiographs", Acta orthopaedica, August 2014, Vol. 85(4), pp. 389-95). For example, a clinician might have to make mental corrections for the incorrect view, which may not be accurate.

One solution to this problem is suggested by Tannast et al. (2008) (Tannast, Moritz; Mistry, Sapan; Steppacher, Simon D.; Reichenbach, Stephan; Langlotz, Frank; Siebenrock, Klaus A.; Zheng, Guoyan, "Radiographic analysis of femoroacetabular impingement with Hip 2 normreliable and validated", Journal of Orthopaedic Research, September 2008, Vol. 26(9), pp. 1199-1205) for radiographic examination of the human pelvis. The software Hip2Norm uses knowledge of the radiographic projection and the anatomy to produce, based on regular radiographs, line drawings of the pelvis and of the acetabular rim as they would be seen on a true AP radiograph, so as to allow standardized evaluation of radiographic parameters for the description of acetabular morphology.

An alternative solution is suggested in WO 2011/098895 A 2. This publication describes a method of registering and adjusting a 3-dimensional multi-object statistical model to one or more standard radiographs in order to obtain a three-dimensional (3D) reconstruction of the anatomy for diagnosis purposes.

A main drawback with both such solutions is that they present the corrected information about the patient's anatomy in a way with which clinicians are unfamiliar. A 2D line drawing still requires the clinician mentally combining the shapes of the lines with the visual information of the radiograph, and a 3D model of the anatomy does not easily allow clinicians to perform the diagnostic steps that they are used to performing on 2D radiographs.

Certain embodiments herein comprise a method that builds on and expands on principles from both publications to modify original regular radiographs to show the anatomy in a normalized position (e.g., desired position and orientation) and still contain the visual information used for diagnosis/planning that is present in the original unmodified radiographs.

SUMMARY

Certain embodiments provide a computer-implemented method of generating a computer-based radiographic representation of at least part of one anatomical object. The method includes obtaining, at a computing device, one or more radiographs of at least part of one anatomical object, each of the one or more radiographs comprising a 2D visual representation of the at least part of one anatomical object in a projection plane. The method further includes obtaining, by the computing device, information indicative of a normalized projection comprising information indicative of a desired position and orientation of the at least part of one anatomical object with respect to the projection plane. The method further includes generating, by the computing device, a 3D model of the at least part of one anatomical object based on the one or more radiographs. The method further includes positioning, by the computing device, the 3D model based on the information indicative of the normalized projection. The method further includes generating, by the computing device, a 2D projection of the 3D model onto the projection plane. The method further includes generating, by the computing device, one or more modified radiographs of the at least part of one anatomical object based on the 2D projection.

Certain embodiments provide a non-transitory computer-readable medium having computer-executable instructions stored thereon, which, when executed by a processor of a computing device, cause the computing device to perform the described method.

Certain embodiments provide a computing device comprising a memory and a processor configured to perform the described method.

DETAILED DESCRIPTION OF CERTAIN INVENTIVE EMBODIMENTS

Certain embodiments herein provide systems and methods for generating a computer-based radiographic representation of at least one anatomical object. For example, the anatomical object may include one or more anatomy/anatomical parts (e.g., hip, knee, shoulder, etc.) of a human, such as one or more bones corresponding to or associated with one or more anatomy parts of a human. In particular, in certain embodiments the computer-based radiographic representation is generated based on one or more actual radiographs containing visual information of the anatomical object, and a 3D model of the anatomical object generated based on the one or more actual radiographs. It should be noted that in certain embodiments, one or more of the methods described herein is a computer-implemented method. For example, computer-based images necessarily need to be generated on a computing device and the generation of such images is a computer centric problem. In particular, such images cannot be generated mentally or by a human alone without a computing device. Further, certain steps may be performed automatically, manually by a user of a computing device, or partially manually and partially automatically such as based on input from a user of a computing device. Further, in certain embodiments, a user may be a person, such as a clinician, engineer, technician, medical professional, etc., that may use a computing device to, or the computing device itself may automatically perform one or more steps of one or more methods described herein.

Embodiments described herein provide a technical solution to a technical problem. In particular, as discussed, due to the limitations of traditional medical imaging, it is not always feasible to take radiographs of anatomical objects in different orientations. Accordingly, radiographic images of anatomical objects are not able to be produced in certain orientations needed to plan medical procedures. Therefore, present medical imaging techniques and medical procedures suffer from the technical problem of not being able to produce radiographic images in the needed orientations. Certain embodiments provided herein provide a technical solution to this technical problem. In particular certain embodiments provide specific techniques to generate radiographs for visualization (e.g., on computing systems) of anatomical objects repositioned in the radiographs to different orientations than the original radiograph. The generated radiographs beneficially provide features of the original radiograph accurately repositioned in the generated radiograph, thereby improving the technical field of medical imaging.

Figure 1:
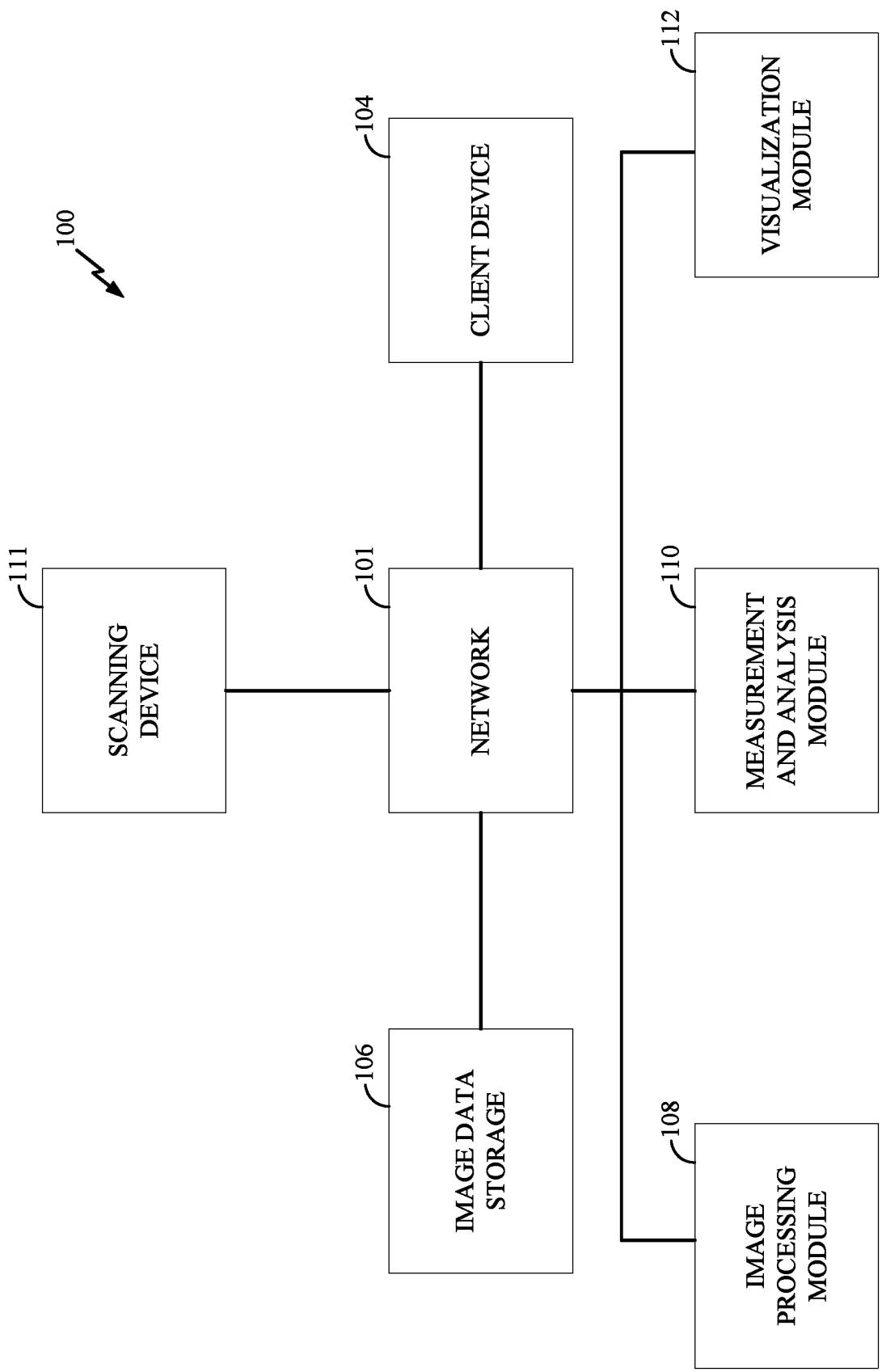
FIG. 1 is a block diagram of one example of a computing environment suitable for practicing various embodiments disclosed herein.

The systems and methods described herein may be implemented in a computing environment comprising one or more computing devices configured to provide various functionalities. FIG. 1 is an example of a computer environment 100 suitable for implementing certain embodiments described herein. The computer environment 100 may include a network 101. The network 101 may take various forms. For example, the network 101 may be a local area network installed at a surgical site. In some embodiments, the network 101 may be a wide area network such as the Internet. In other embodiments, the network 101 may be a combination of local area networks and wide area networks. Typically, the network will allow for secured communications and data to be shared between various computing devices. Among these computing devices are a client device 104. The client device 104 may be a typical personal computer device that runs an off-the-shelf operating systems such as Windows, Mac OS, Linux, Chrome OS, or some other operating system. The client device 104 may have application software installed to allow it to interact via the network 101 with other software stored on various other modules and devices in the computing environment 100. This application software may take the form of a web browser capable of accessing a remote application service. Alternatively, the application software may be a client application installed in the operating system of the client device 104. Client device 104 may also take the form of a specialized computer, specifically designed for medical imaging work, or even more specifically for generating a computer-based radiographic representation of at least one anatomical object. The client device 104 may further take the form of a mobile device or tablet computer configured to communicate via the network 101 and further configured to run one or more software modules to allow a user to perform various methods described herein.

The computer environment 100 may further include image data storage 106. Typically, the image data storage 106 takes the form of a database designed to store image files captured by a scanning device 111 (e.g., X-ray imaging device). These images may be Digital Imaging and Communications in Medicine (DICOM) images, or other types of images. The image data storage 106 may be part of a scanning device 111, or alternatively it may be part of a client computing device 104. The image data storage 106 may also be in a standalone database having dedicated storage optimized for medical image data. The image data store 106 may further include in the same database or a separate database 2-D and or 3-D digital representations/images of designs implants, as further discussed herein. The computer environment 100 may also include a scanning device 111. The scanning device 111 may typically be a medical imaging device which scans/images a patient to create images of their anatomy. In the computing environment 100 shown in FIG. 1, the scanning device 111 may be an X-ray device that generates 2D radiographs, as discussed.

As will be explained in detail below, the scanning device 111 may be configured to create 2D radiographic images, referred to as radiographs, of anatomical objects. Those images may be stored in the image data storage 106, and utilized to create 3D models of the anatomical objects. The 3D models are further used to generate modified radiographs of the anatomical objects including the anatomical objects in different positions than the original radiographs. To that end, the computing environment 100 may also include an image processing module 108. The image processing module 108 may take the form of computer software, hardware, or a combination of both which retrieves the medical imaging data from image data storage 106 and generates 3D models and modified radiographs as further discussed herein. In some embodiments, the image processing module 108 may be provided via a web-based network application that is accessed by a computer over the network (such as client device 104, for example). Alternatively, the image processing module may be a software application that is installed directly on the client device 104, and accesses image data storage 106 via the network 101. In general, the image processing module 108 may be any combination of software and/or hardware located within the computing environment 100 which provides image processing capabilities on the image data stored within the image data storage 106.

The computing environment also may include a measurement and analysis module 110 ("measurement and analysis module"). The measurement and analysis module 110 may be software that is complementary to and/or bundled with the image processing module 108. The measurement and analysis module may be an application configured to determine measurements of anatomical objects, such as in 3D models of the anatomical objects such as those generated according to the techniques discussed herein. As with the image processing module 108, the measurement and analysis module 110 may be a network-based application which is accessed via a web browser by one or more client devices 104. It may also be a native application installed into the operating system of a computer such as, client device 104 for example. In still other embodiments, the measurement and analysis module 110 may be a network application which is run as a client/server implementation.

The computing environment also may include a visualization module 112. The visualization module 112 may be software that is complementary to and/or bundled with the image processing module 108. The visualization module 112 may be an application configured to provide different visualizations of anatomical objects. For example, visualization module 112 may cause one or more 3D models and/or or radiographs (e.g., modified or original) to be displayed on a display of a computing device, such as client device 104, by rendering images for display. Visualization module 112, as will be discussed, may render images with different colors, sizes, according to different user interfaces, etc. for display. Visualization module 112 may further render images overlaid on top of other images, such as images or renders (e.g., 2D or 3D) of implants on anatomical objects, as further discussed herein. As with the image processing module 108, the visualization module 112 may be a network-based application which is accessed via a web browser by one or more client devices 104. It may also be a native application installed into the operating system of a computer such as, client device 104 for example. In still other embodiments, the visualization module 112 may be a network application which is run as a client/server implementation.

Figure 2:
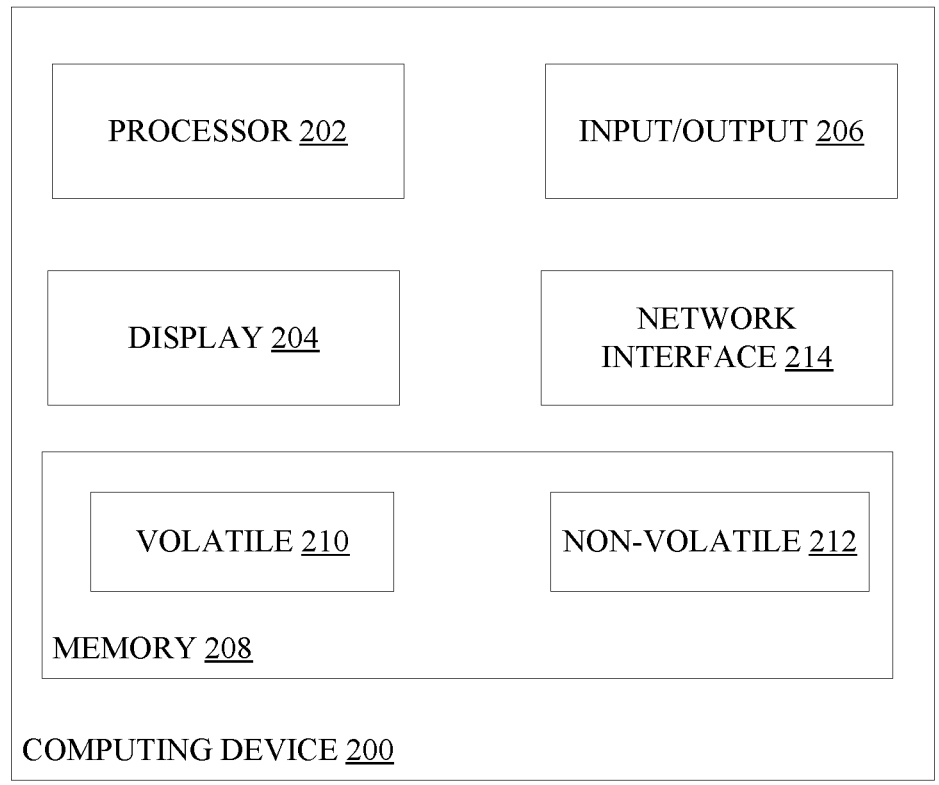
FIG. 2 is a high level system diagram of a computing system that may be used in accordance with one or more embodiments.

Various embodiments of the invention may be implemented using general and/or special purpose computing devices. Turning now to FIG. 2, an example of a computing device 200 suitable for implementing various embodiments of the invention is shown. The computer system 200 may generally take the form of computer hardware configured to execute certain processes and instructions in accordance with various aspects of one or more embodiments described herein. The computer hardware may be a single computer or it may be multiple computers configured to work together. The computing device 200 includes a processor 202. The processor 202 may be one or more standard personal computer processor such as those designed and/or distributed by Intel, Advanced Micro Devices, Apple, or ARM. The processor 202 may also be a more specialized processor designed specifically for image processing and/or analysis. The computing device 200 may also include a display 204. The display 204 may be a standard computer monitor, such as an LCD monitor as is well known. The display 204 may also take the form of a display integrated into the body of the computing device, for example as with an all-in-one computing device or a tablet computer.

The computing device 200 may also include input/output devices 206. These may include standard peripherals such as keyboards, mice, printers, and other basic I/O software and hardware. The computing device 200 may further include memory 208. The memory 208 may take various forms. For example, the memory 208 may include volatile memory 210. The volatile memory 210 may be some form of random access memory, and may be generally configured to load executable software modules into memory so that the software modules may be executed by the processor 202 in a manner well known in the art. The software modules may be stored in a nonvolatile memory 212. The non-volatile memory 212 may take the form of a hard disk drive, a flash memory, a solid state hard drive or some other form of non-volatile memory. The non-volatile memory 212 may also be used to store non-executable data, such database files and the like.

The computer device 200 also may include a network interface 214. The network interface may take the form of a network interface card and its corresponding software drivers and/or firmware configured to provide the system 200 with access to a network (such as the Internet, for example). The network interface card 214 may be configured to access various different types of networks, such as those described above in connection with FIG. 1. For example the network interface card 214 may be configured to access private networks that are not publicly accessible. The network interface card 214 may also be configured to access wireless networks such using wireless data transfer technologies such as EVDO, WiMax, or LTE network. Although a single network interface 214 is shown in FIG. 2, multiple network interface cards 214 may be present in order to access different types of networks. In addition, a single network interface card 214 may be configured to allow access to multiple different types of networks.

In general, the computing environment 200 shown in FIG. 2 may generally include one, a few, or many different types of computing devices 200 which work together to carry out various embodiments described below. A skilled artisan will readily appreciate that various different types of computing devices and network configurations may be implemented to carry out the inventive systems and methods disclosed herein.

Figure 3:
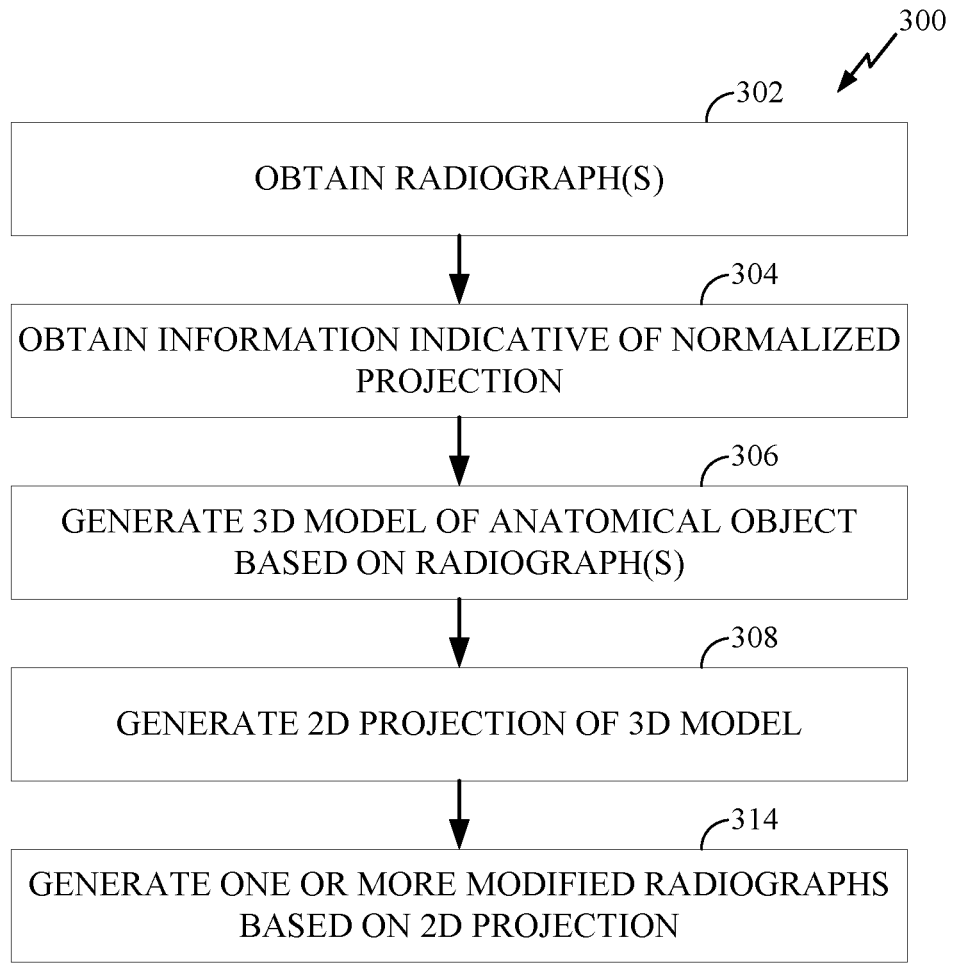
FIGS. 3 and 3A illustrate a flow chart showing a process for generating a computer-based radiographic representation of at least one anatomical object, according to certain embodiments.

FIG. 3 illustrates a flow chart showing a process 300 for generating a computer-based radiographic representation of at least one anatomical object according to certain embodiments. It should be noted that in certain embodiments, process 300 is a computer-implemented process. Further, certain blocks may be performed automatically, manually by a user of a computing device, or partially manually and partially automatically such as based on input from a user of a computing device.

Figure 4:
FIG. 4 illustrates an example radiograph of a proximal femur and part of a pelvis.

Process 300 begins at block 302, wherein one or more radiographs of at least one anatomical object are obtained. In certain aspects, the one or more radiographs may be for at least part of the at least one anatomical object and the techniques described herein may be similarly applied to at least part of at least one anatomical object and not necessarily complete anatomical objects. The radiographs may be acquired using the scanning device 111 shown in FIG. 1, such as an X-ray scanner. Each radiograph includes a 2D visual representation of the at least one anatomical object in a projection plane. In certain embodiments, the projection plane corresponds to a plane of a detector of the X-ray scanner. The radiograph (or radiographs) acquired using the scanning device 111 may be stored in image data storage 106 or some other computer memory accessible via the computer network 101. Obtaining the radiographs may refer to acquiring the radiographs using the X-ray scanner, and/or retrieving the radiographs from memory. FIG. 4 illustrates an example radiograph 400 of a proximal femur and part of a pelvis. As shown, the AP view of the femur is not clear in radiograph 400. In particular, the femur is rotated, flexed, and adducted.

In certain embodiments, the radiographs can be regular 2D radiographs obtained by projecting a beam of X-rays from a source through the anatomy of a patient onto a detector. The radiographs may contain visual information of one or more anatomical objects corresponding to one or more anatomy parts of interest. In certain embodiments, the radiographs include information from a locating/scaling device to determine the scaling factor and/or determine the position and/or orientation of the patient with respect to the X-ray detector plane. This information can be used to determine the position of the source and/or an anatomical object with respect to the projection plane (e.g., corresponding to the detector). Alternatively such information can be obtained separately.

The process then moves to block 304. At block 304, information indicative of a normalized projection (e.g., a definition of a normalized projection) is obtained for the at least one anatomical object. In certain embodiments, the information indicative of a normalized projection comprises information indicative of a desired position and orientation of the at least one anatomical object relative to the projection plane. In certain embodiments, the information indicative of a normalized projection further comprises information indicative of the source (e.g., information indicative of the location of the source) of the X-rays used to generate the radiographs with respect to the projection plane (e.g., information indicative of the projection source (e.g., location of the projection source) of the X-ray machine). In certain embodiments, the position and orientation of an anatomical object can be defined in terms of its anatomical coordinate system. The information indicative of a normalized projection may be stored on and obtained from a memory, such as image data storage 106 or another memory. The information indicative of a normalized projection may be generated by a user, such as using a computing device, such as client device 104 or another computing device.

The process continues to block 306. At block 306, a 3D model of the at least one anatomical object is generated based on the one or more radiographs. For example, image processing module 108 generates the 3D model (also referred to as a virtual 3D model). In certain embodiments, the 3D model is generated from a deformable 3D model including statistical information (e.g., one or more of statistical shape model, articulated statistical shape model, active shape model, appearance model, intensity model, etc.) about the at least one anatomical object. In certain embodiments, the 3D model is generated by registering and adjusting a shape of the deformable 3D model to align with a shape of the at least one anatomical object in the one or more radiographs according to the visual information (e.g., 2D visual representation of the at least one anatomical object) in the one or more radiographs. In certain embodiments, the 3D model is generated accordingly to known methods in the art, such as those described in Balestra et al. (2014) (S. Balestra, S. Schumann, J. Heverhagen, L. Nolte, and G. Zheng, "Articulated Statistical Shape Model-Based 2D-3D Reconstruction of a Hip Joint", in: Information Processing in Computer-Assisted Interventions, Proceedings of IPCAI 2014, June 2014, pp. 128-137). In certain embodiments, the 3D model is at least one virtual 3D model of the at least one anatomical object. For example, the 3D model may comprise separate virtual 3D models for each of the anatomical objects.

Figure 5:
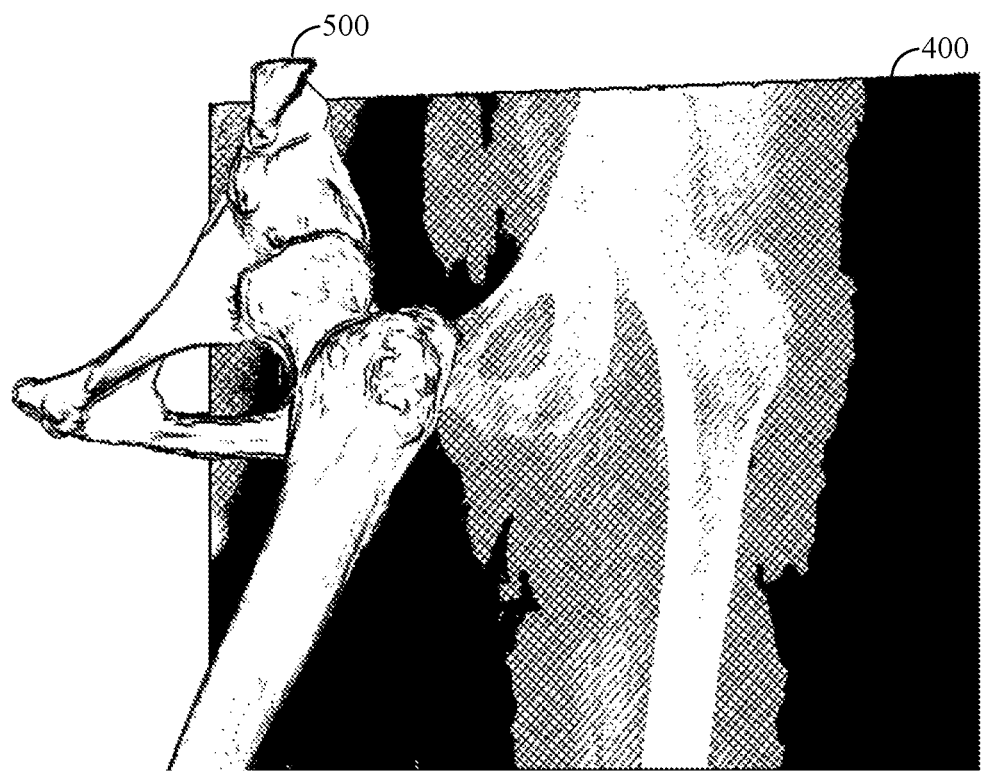
FIG. 5 illustrates an example of a 3D model of at least one anatomical object generated from the radiograph of FIG. 4.

FIG. 5 illustrates an example of a 3D model 500 of at least one anatomical object generated from radiograph 400 of FIG. 4. In particular, the 3D model 500 corresponds to the part of the pelvis and femur from FIG. 4. As shown, in 3D model 500, the pelvis is correctly oriented with respect to a projection plane of the radiograph 400 for an AP view. However, in 3D model 500, the femur is internally rotated, slightly adducted, and in flexion.

Figure 3A:
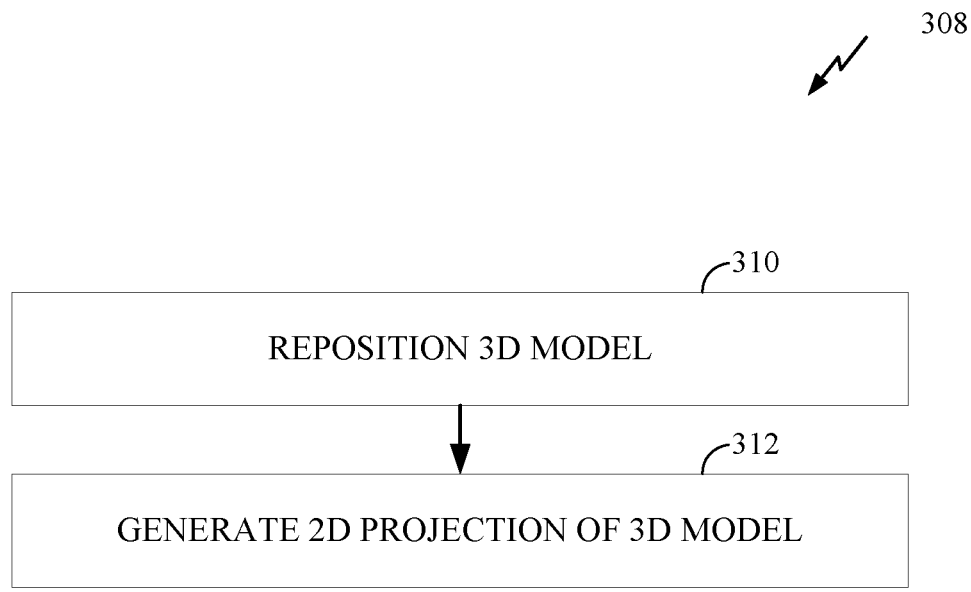

Continuing at block 308, a 2D projection of the 3D model of the at least one anatomical object is generated. For example, image processing module 108 generates the 2D projection. In certain aspects, as further discussed herein, the 2D projection can be a contour line representation and/or synthetic radiograph. In certain embodiments, block 308 comprises blocks 310 and 312, shown in FIG. 3A.

At block 310, the 3D model (e.g., one or more virtual 3D models) is repositioned (e.g., with respect to the projection plane, an optimal plane, other objects/anatomy, etc.). For example, the 3D model is repositioned automatically by, or by a user using, image processing module 108. In certain embodiments, the 3D model is also repositioned with respect to the source of the X-rays. The 3D model (e.g., each of the one or more virtual 3D models) may include the definition of an anatomical coordinate system, and the 3D model position may be defined with respect to the anatomical coordinate system. In certain embodiments, the anatomical coordinate system is defined based on landmarks (e.g., known anatomical features) that exist in a 3D statistical model of the at least one anatomical object used to create the 3D model, the landmark positions following the shape adjustment discussed with respect to block 306. In certain embodiments, the anatomical coordinate system is defined based on landmarks that are automatically or manually identified on the 3D model.

The repositioning of block 310 may be performed so that a new position and orientation of the 3D model correspond to the information indicative of the normalized projection described in block 304. If the 3D model includes multiple anatomy parts, normal articulation of the anatomy parts may be respected during the repositioning. Such normal articulation may be expressed as explicit rules for repositioning (e.g. rotation around the center of rotation of the femoral head), or as part of the deformable 3D model used to generate the 3D model as discussed at block 306. It should be noted that in certain aspects block 310 is optional and the 3D model is not repositioned.

Figure 6:
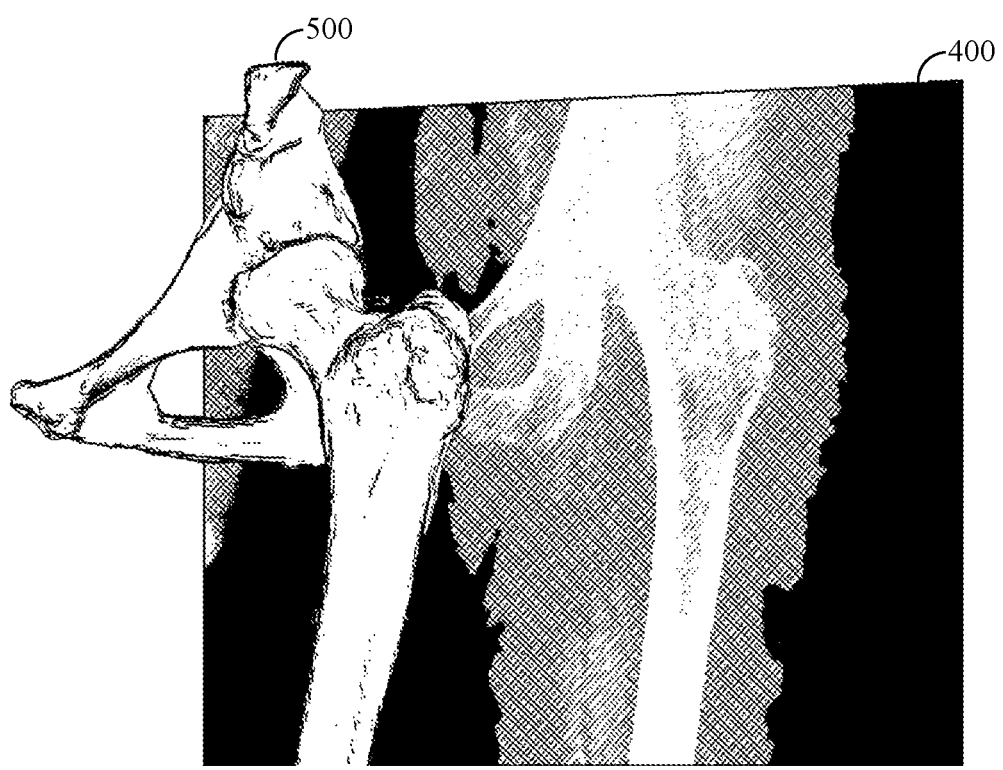
FIG. 6 illustrates an example of the 3D model of FIG. 5 repositioned.

FIG. 6 illustrates an example of the 3D model 500 of FIG. 5 repositioned. In particular, the 3D model 500 corresponds to a position and orientation (e.g., referred to as a normalized position) of the 3D model 500 of the femur with respect to the projection plane of the radiograph 400 adjusted in order to obtain a true AP view. The position and orientation of the pelvis are maintained. The correction is made while respecting the normal articulation of the different anatomy parts.

At block 312, a 2D projection of the 3D model onto a plane (e.g., projection plane, optimal plane, etc.) is generated. In some embodiments, the 2D projection is generated by image processing module 108 automatically tracing, or a user of image processing module 108 causing it to trace, rays from a position of a source of x-rays used to generate the one or more radiographs with respect to the plane along points of the 3D model that are tangential to a surface of the 3D model. The resulting 2D projection may comprise a contour line representation.

Figure 7:
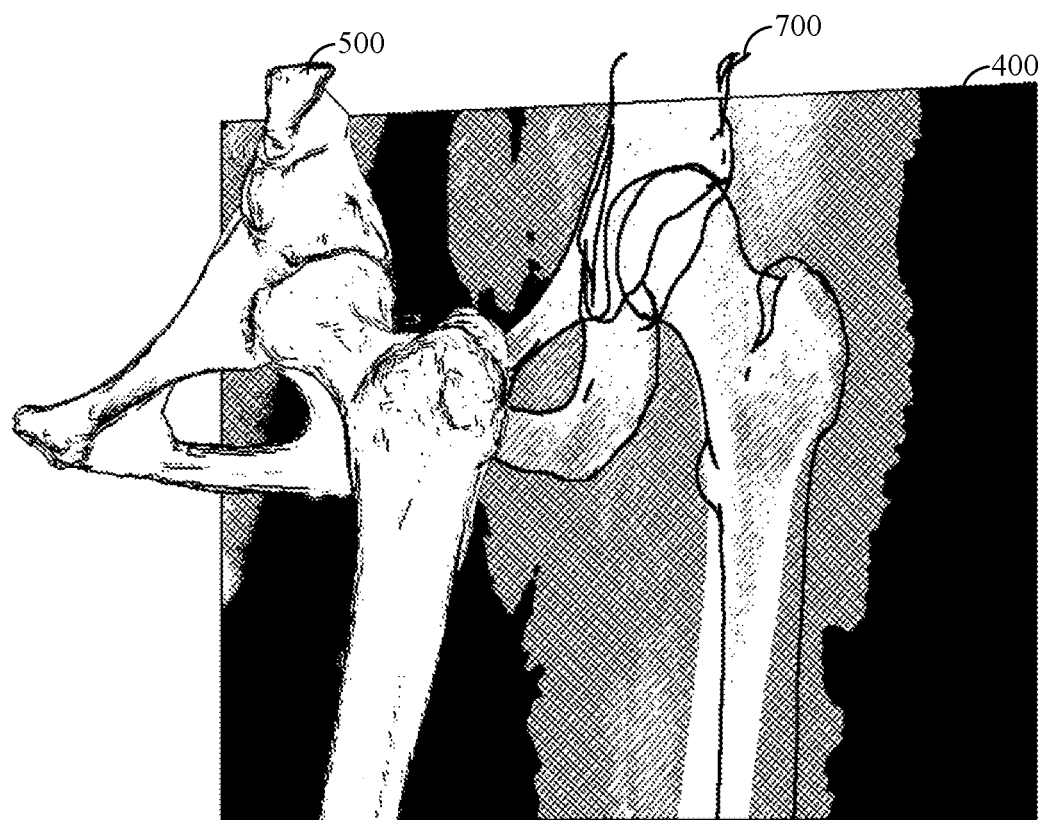
FIGS. 7 and 8 illustrate an example of a 2D projection as a contour line representation.
Figure 8:
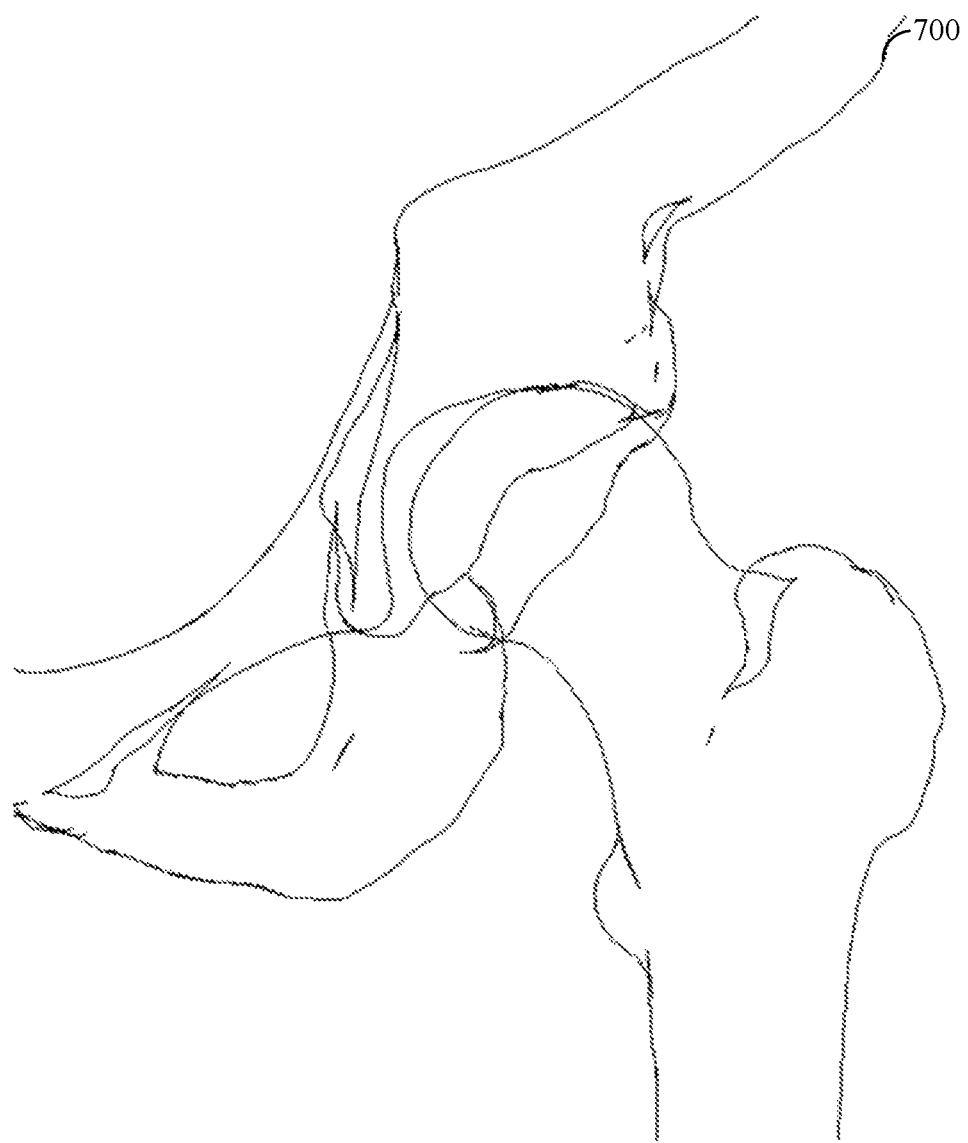

FIGS. 7 and 8 illustrate an example of the 2D projection as a contour line representation 700. In particular, the contours of the 3D model 500 in the normalized position are projected onto the projection plane of the radiograph 400, by tracing rays through the source of the X-rays of the radiograph 400 along all surface points in which the surfaces are tangential to the rays resulting in contour representation 700.

In some other embodiments, the 2D projection is generated by image processing module 108 automatically, or a user of image processing module 108 causing it to, trace rays from a position of a source of x-rays used to generate the one or more radiographs with respect to the projection plane through one or more pixels of the projection plane, and for each of the one or more pixels, determine a grey value for the pixel based on a length of a ray associated with the pixel that is included within the 3D model. The resulting 2D projection may be referred to as a synthetic radiograph containing the grey values. In certain aspects, the grey value for each pixel is further based on an attenuation factor. In certain embodiments, the attenuation factor is included in the deformable 3D model used to generate the 3D model as discussed at block 306. If the 3D model includes multiple virtual 3D models, the attenuation factor may be different for different 3D models (e.g., corresponding to different anatomical objects). In certain embodiments, the deformable 3D model includes an attenuation factor that varies through 3D space. In certain embodiments, the deformable 3D model includes an attenuation factor that varies along the surface normal of its surfaces. Different approaches to storing/assigning attenuation factors in a deformable 3D model can be combined.

Figure 9:
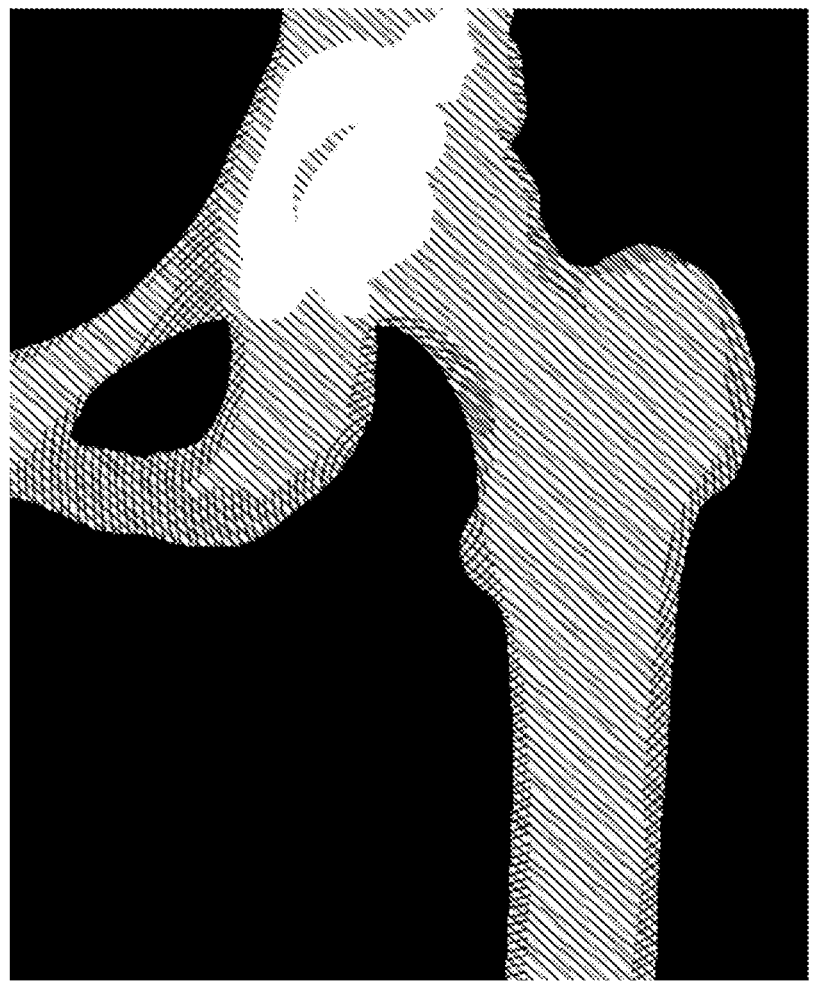
FIG. 9 illustrates an example of a 2D projection as a synthetic radiograph.

FIG. 9 illustrates an example of the 2D projection as a synthetic radiograph.

Continuing at block 314, one or more modified radiographs of the at least one anatomical object are generated based on the 2D projection. The one or more modified radiographs may be generated (e.g., automatically) by image processing module 108. In certain embodiments, such as if the 2D projection is a contour line representation, the one or more modified radiographs are generated by identifying one or more projected contours of the at least one anatomical object in the 2D projection, and morphing the one or more radiographs to align one or more contours of the at least one anatomical object in the one or more radiographs to the one or more projected contours. For example, based on the visual information of the at least one anatomical object, outer and optionally inner contours of each of the anatomical objects may be identified in the one or more radiographs. For example, contours of the at least one anatomical object may be identified or detected using known methods in the art such as those described in Chen et al. (2014) (Chen, C.; Xie, W.; Franke, J.; Grutzner, P. A.; Nolte, L.-P.; Zheng, G., "Automatic X-ray landmark detection and shape segmentation via data-driven joint estimation of image displacements", Medical Image Analysis, April 2014, Vol. 18(3), pp. 487-499). The one or more radiographs may be morphed (e.g., changed smoothly from one image to another by small gradual steps using computer animation techniques) so that the identified contours in the one or more radiographs align with (e.g., best match) the projected contours (e.g., the contour line representation of the 2D projection), such as using image morphing techniques.

Figure 10:
FIG. 10 illustrates an example of the radiograph of FIG. 4 with contours of the at least one anatomical object identified.
Figure 11:
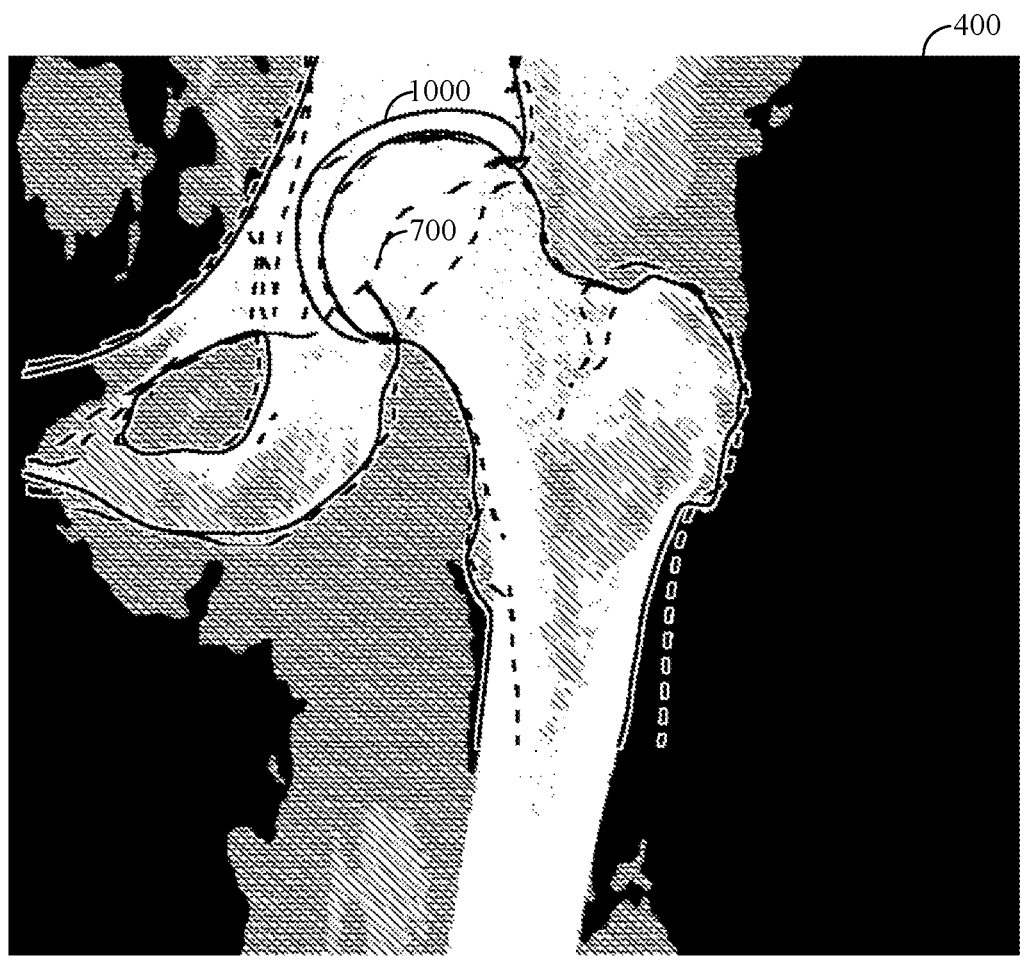
FIG. 11 illustrates an example of the radiograph of FIG. 4 with both contours of FIG. 10 and contour representation of FIGS. 7 and 8 overlaid on the radiograph.
Figure 12:
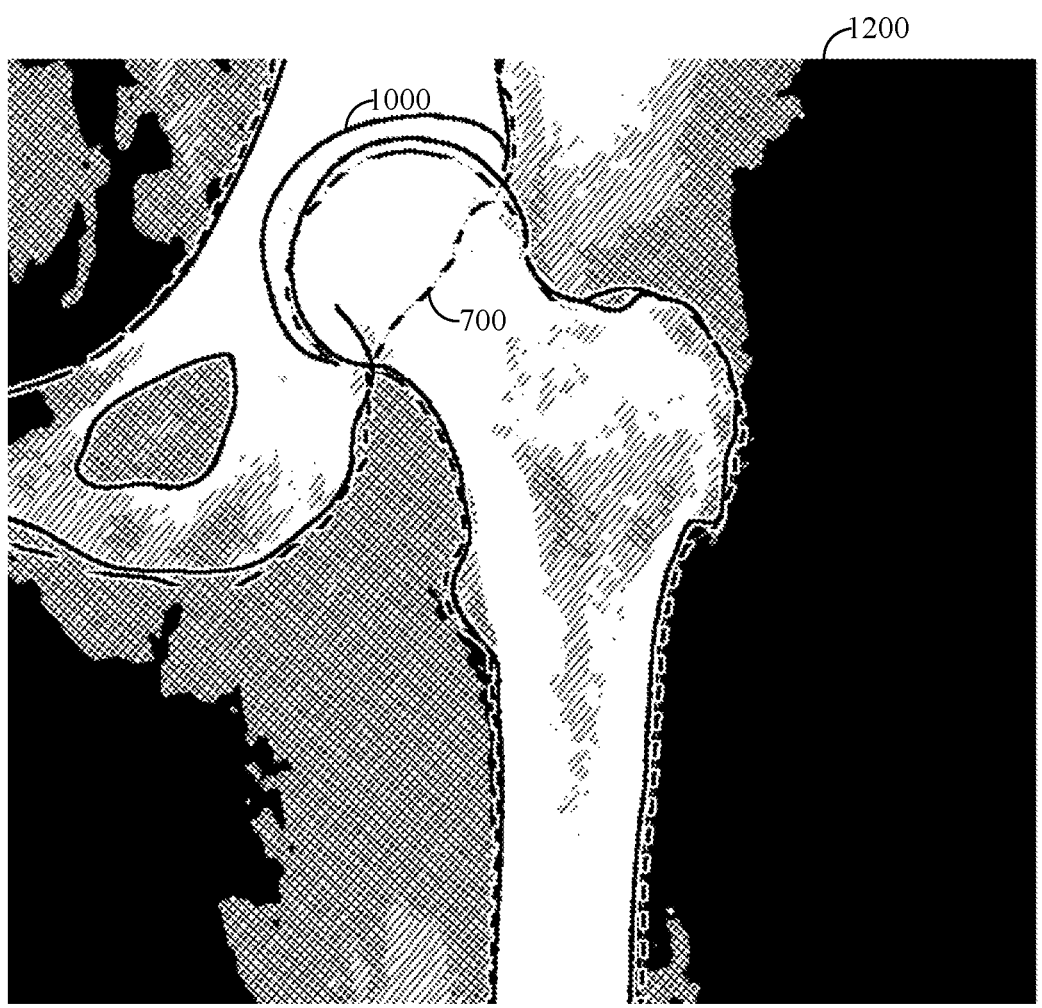
FIG. 12 illustrates an example of a modified radiograph that is a morph of the radiograph of FIG. 10 such that the contours of FIG. 10 align with the contour representation of FIGS. 7 and 8.

FIG. 10 illustrates an example of the radiograph 400 with contours 1000 of the at least one anatomical object identified. FIG. 11 illustrates an example of the radiograph 400 with both contours 1000 and contour representation 700 overlaid on radiograph 400. FIG. 12 illustrates an example of a modified radiograph 1200 that is a morph of radiograph 400 of FIG. 10 such that the contours 1000 align with the contour representation 700.

In certain embodiments, such as if the 2D projection is a synthetic radiograph, the one or more modified radiographs are generated by performing non-rigid image registration techniques to register the one or more radiographs to the 2D projection. The non-rigid image registration techniques may be done according to known methods in the art such as those described in Crum et al. (2004) (Crum, W R; Hartkens, T; Hill, D L G, "Non-rigid image registration: theory and practice", The British journal of radiology, 2004, Vol. 77 Spec No 2, pp. S140-53). In certain aspects, an original synthetic radiograph may be generated based on the 3D model before repositioning at block 310. This original synthetic radiograph may be registered to the synthetic radiograph generated at block 312 referred to as a repositioned synthetic radiograph. The transformation for registering the original radiograph to the repositioned synthetic radiograph may be stored/recorded, and then applied to the original one or more radiographs to generate the one or more modified radiographs.

Figure 13:
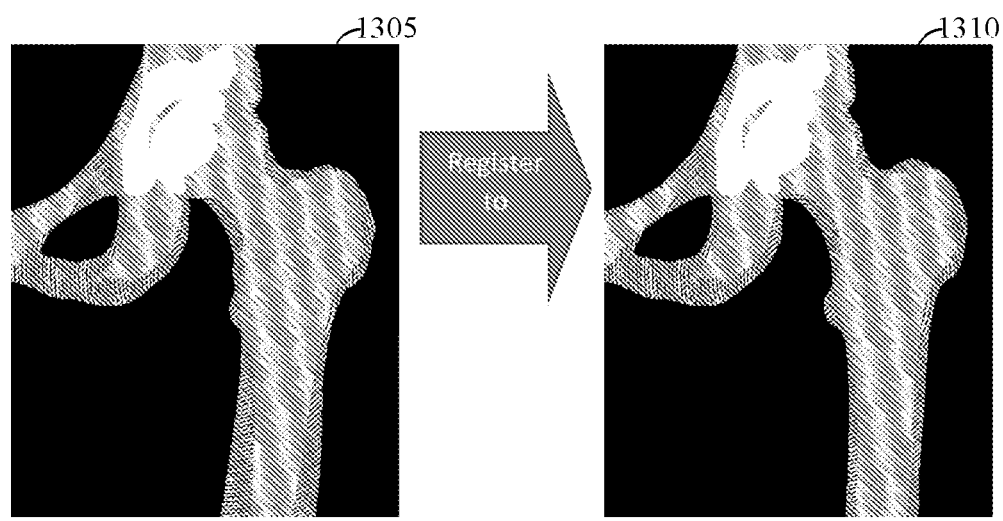
FIG. 13 illustrates an example of an original synthetic radiograph which is to be registered to a repositioned synthetic radiograph.
Figure 14:
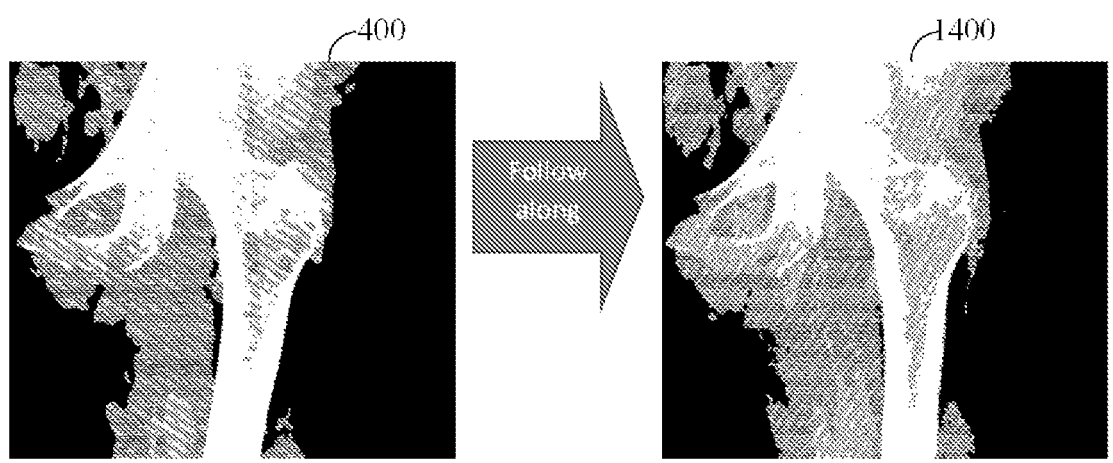
FIG. 14 illustrates an example of an original radiograph and a modified radiograph.

FIG. 13 illustrates an example of an original synthetic radiograph 1305 which is to be registered to repositioned synthetic radiograph 1310. FIG. 14 illustrates an example of an original radiograph 400, and a modified radiograph 1400. Modified radiograph 1400 is generated by applying the same transformations as used to register original synthetic radiograph 1305 to repositioned synthetic radiograph 1310.

In certain embodiments, the one or more modified radiographs are generated by using a 2D transformation (e.g., based on one or more landmarks of the at least one anatomical object) on the one or more radiographs to align one or more landmarks of the at least one anatomical object in the one or more radiographs to the 2D projection.

In certain embodiments, the one or more modified radiographs are generated by using a non-uniform scaling on the one or more radiographs to align the at least one anatomical object in the one or more radiographs to the 2D projection.

Figure 15:
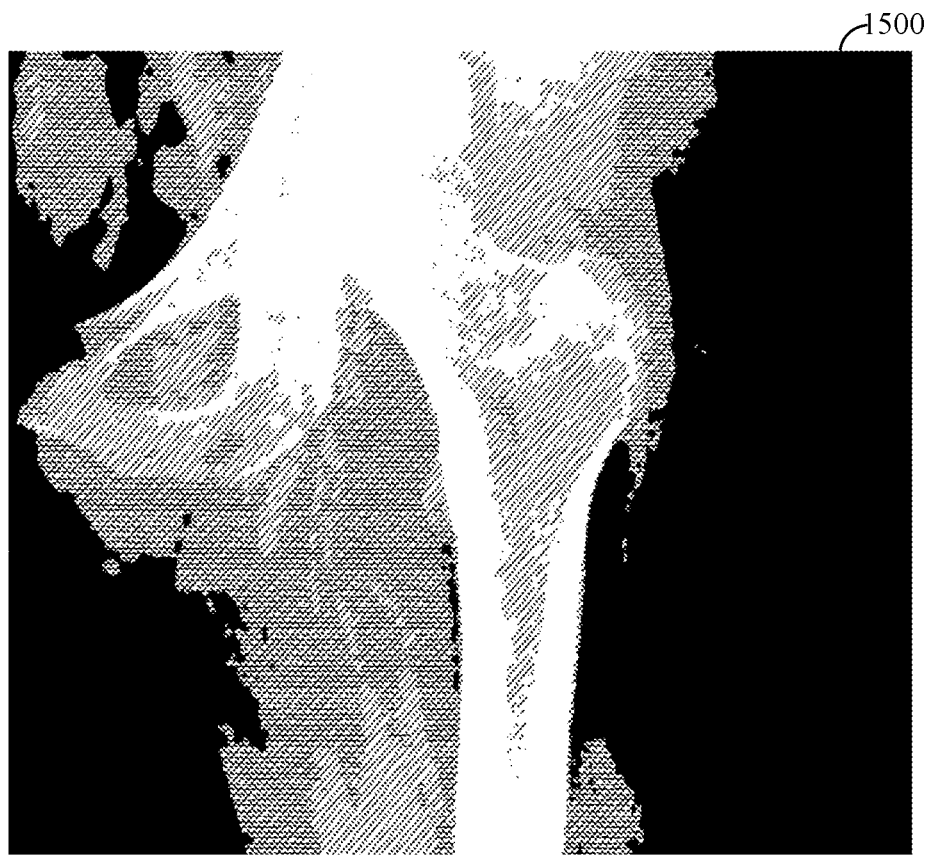
FIG. 15 illustrates an example of a modified radiograph.

Accordingly, process 300 can be performed to generate one or more modified radiographs in desired positions. FIG. 15 illustrates an example of a modified radiograph 1500.

Certain embodiments herein further provide systems and methods that use one or more steps of generating one or more modified radiographs. For example, certain embodiments further provide systems and methods for 2D templating. 2D templating refers to selecting an appropriate (e.g., most appropriate) brand, type, shape, and/or size of implant, such as from a library of implants (e.g., stored as digital representations on a storage coupled to network 100), by overlaying a two-dimensional medical image of an anatomical object with a representation (e.g., a line drawing, contour drawing, projection of a 3D model, shaded area drawing, etc.) of an implant from the library, which is represented (e.g., drawn) at the correct scale and orientation appropriate for a given view of the anatomy. As described above, the view of the anatomy in a radiograph as achieved by the radiologist might not correspond to the ideal view that is intrinsic to the 2D line drawings or contours drawings (or other types of templates) of implants of the implant library. This might lead to an inappropriate selection of implant.

As discussed, visualization module 112 may be configured to display a modified or enhanced view of anatomy to aid in 2D templating. For example, the visualization module 112 may be configured to display on a display of computing device 104 a modified radiograph according to process 300. In certain embodiments, the normalized projection used in process 300 corresponds to the ideal view that is intrinsic to the implant templates of the implant library. Accordingly, a user can more accurately utilize the implant templates on the modified radiograph to select an appropriate implant. For example, for the 2D templating of the femoral component of a hip implant, if the femur is externally rotated in the original radiograph, in certain embodiments, it will be displayed in that radiograph with a reduced neck length. The user might therefore be inclined to select a small implant. The modified radiograph, in certain embodiments, can display the femur without external rotation and therefore the correct neck length. The user can therefore have a higher chance of selecting an appropriate-size implant.

In some embodiments, visualization module 112 is configured to display a repositioned synthetic radiograph instead of the modified radiograph according to process 300. Such a repositioned synthetic radiograph can also display the anatomy in the normalized projection, but does not have the full greyscale information that the original radiograph has. However, for 2D templating, it can still lead to more accurate measurements and a better implant selection.

In some embodiments, visualization module 112 is configured to display modified or synthetic radiographs (e.g., modified radiographs or repositioned synthetic radiographs or synthetic radiographs that have not been repositioned) with a visual indication to draw attention to the fact that the user is not looking at the original radiograph but at a modified or synthetic image. This visual indication can be a watermark, a letter, a drawing, an image border, etc., and can be in a contrasting color. Alternatively, the visual indication can be a color shift (e.g. whereas the original radiograph is displayed in grayscale colors, modified or synthetic radiographs can be displayed in tones of another color, such as red, green, orange, blue, yellow, pink, cyan, magenta, purple, violet, etc.). Alternatively the grayscale colors can be inverted. Alternatively other known image-processing operations or filters can be applied as visual indication. Other visual indications are possible.

In some embodiments, visualization module 112 is configured to display at a time a combination of two or more of the original radiograph, one or more modified radiographs, and one or more synthetic radiographs. Each of the images may be displayed with a visual indication to draw attention to the type of image, and possibly the normalized view that is displayed in the image.

In some embodiments, visualization module 112 is configured to display standard anatomical measurements on or in the display area surrounding one or more of the original radiograph, a modified radiograph, and a synthetic radiograph. For example, image processing module 108 may perform blocks 302 and 304 to generate a 3D model of at least one anatomical object from a radiograph. Image processing module 108 can further define one or more landmarks and/or an anatomical coordinate system associated with the at least one anatomical object in the 3D model, such as discussed with respect to block 310. Measurement and analysis module 110 may be configured to perform one or more measurements (e.g., standard anatomical measurements) of the at least one anatomical object in the 3D model based on the one or more anatomical landmarks or the anatomical coordinate system. Then, visualization module 112 can display the one or more measurements on or in the display area surrounding one or more of the original radiograph, a modified radiograph, and a synthetic radiograph.

Accordingly, measurements can be displayed that are not possible to obtain directly from a 2D medical image, or measurements that cannot be obtained in an accurate way from a 2D medical image, such as measurements in directions that are not parallel to the projection plane.

In some embodiments, the 2D templating is for hip replacement surgery. In such embodiments, the one or more measurements can comprise one or more of femoral diameter, femoral neck length, femoral offset, acetabulum diameter, acetabulum depth, acetabulum inclination, acetabulum anteversion, pelvic tilt, tilt of the coronal reference plane of the pelvis, pelvic anterior tilt, pelvic lateral tilt, pelvic rotation, neck-shaft angle, femoral torsion (also known as anteversion), femur length, leg length, and/or angles defining the position of the joint in the image (e.g., adduction/abduction, internal/external rotation and/or flexion/extension).

In some embodiments, the 2D templating is for knee replacement surgery. In such embodiments, the one or more measurements can comprise one or more of femoral mediolateral size, femoral anteroposterior size, femoral medial anteroposterior size, femoral lateral anteroposterior size, tibial mediolateral size, tibial anteroposterior size, tibial medial anteroposterior size, tibial lateral anteroposterior size, varus/valgus angle, femoral shaft angle, and/or angles defining the position of the joint in the image (e.g., adduction/abduction, internal/external rotation and/or flexion/extension).

In some embodiments, the 2D templating is for other types of surgery, such as total or reverse shoulder arthroplasty, ankle arthroplasty, wrist arthroplasty, elbow arthroplasty, osteotomies and/or fracture repair.

In some embodiments, the 3D model and/or deformable 3D model used to generate the 3D model discussed herein includes normative data, e.g. data relating to healthy anatomy. Accordingly, visualization module 112 can not only display anatomical measurements performed on the anatomy of the individual patient as discussed, but also values for those measurements as they would be in a healthy situation. For example, in the case of 2D templating on a hip exhibiting excessive wear of the femur head, visualization module 112 can display the actual femur neck length, the femur neck length as it ought to be in healthy situation, or both. In some embodiments, the normative data is obtained by removing a diseased part of the contour of the anatomy from the 2D model and/or 3D model and reconstructing a remainder of the anatomy (e.g., using statistical shape modelling (SSM)) to obtain the corresponding health 3D shape of the anatomy.

In certain embodiments, the visualization module 112 displays information indicative of the one or more anatomical landmarks and/or anatomical coordinate systems on one or more of the original radiograph, a modified radiograph, and a synthetic radiograph. For example, image processing module 108 may perform blocks 302 and 304 to generate a 3D model of at least one anatomical object from a radiograph. Image processing module 108 can further define one or more landmarks and/or an anatomical coordinate system associated with the at least one anatomical object in the 3D model, such as discussed with respect to block 310. Then, visualization module 112 can display the one or more anatomical landmarks and/or anatomical coordinate systems on one or more of the original radiograph, a modified radiograph, and a synthetic radiograph.

Accordingly, anatomical coordinate systems or landmarks can be displayed that are not possible to obtain directly or accurately from a 2D medical image. In some embodiments, the 3D model and/or deformable 3D model used to generate the 3D model discussed herein includes normative data, e.g. data relating to healthy anatomy. Accordingly, visualization module 112 can not only display landmarks and anatomical coordinate systems where they are in the individual patient, but also where they ought to be in a healthy situation. For example, in the case of 2D templating on a hip exhibiting excessive wear of the femur head, visualization module 112 can display the actual center of rotation, the center of rotation where it ought to be in healthy situation, or both.

In some embodiments, visualization module 112 may be configured to display a 2D template of an implant on the display in an orientation and position relative to the position and orientation of the at least one anatomical object in the one or more modified radiographs.

In some embodiments, visualization module 112 may be configured to display modified or enhanced views of implants on an original radiograph to aid in 2D templating. For example, visualization module 112 can display the original radiograph and a modified radiograph or repositioned synthetic radiograph side-by-side. The visualization module 112 may display the original 2D templates from the implant library on the modified radiograph or repositioned synthetic radiograph, and an adapted representation of the same 2D template on the original radiograph. This adapted representation may take the position of the anatomical parts of interest as they are visible in the original radiograph into account.

For example, the adapted representation of the 2D template may be generated by image processing module 108 inverting the image transformation steps applied to the original radiograph at block 314 to generate the one or more modified radiographs and apply the inverted image transformation steps to the original 2D template to generate the adapted representation of the 2D template.

In particular, in certain embodiments, image processing module 108 generates the one or more modified radiographs of the at least one anatomical object based on the 2D projection by applying a transformation to the one or more modified radiographs to align the one or more modified radiographs with the 2D projection. Accordingly, image processing module 108 applies an inverse of the transformation to a 2D template of the implant. Further, visualization module 112 displays the transformed 2D template of the implant along with the one or more radiographs on a display of the computing device.

In another example, the image processing module 108 can invert the repositioning of the 3D model performed at block 310 and apply it to the original 2D template as placed in the modified radiograph or repositioned synthetic radiograph. Accordingly, the 2D template can be positioned in the 3D space of 3D model before repositioning, such as at block 306. Using information on the position of the source and the projection plane of the original radiograph and/or information about the registration and adjustment of the shape of the deformable 3D model as established in block 306, the 2D template can then be projected onto the original radiograph.

In particular, in certain embodiments, image processing module 108 positions the 3D model with respect to the projection plane by applying a transformation to the 3D model to align with the desired position and orientation of the at least one anatomical object with respect to the projection plane. Accordingly, image processing module 108 applies an inverse of the transformation to a 2D template of the implant as positioned with respect to the one or more modified radiographs to generate a 3D template of the implant positioned with respect to the 3D model. Further, image processing module 108 generates a second 2D projection of the 3D template of the implant onto the projection plane in the one or more radiographs. Further, visualization module 112 displays the second 2D projection on the one or more radiographs on a display of the computing device.

In some embodiments, the library of implants comprises 3D templates of the implants. In some such embodiments, image processing module 108 can project a 3D template onto the original radiograph using the position of the 3D model of the at least one anatomical object and possibly information regarding the source and projection plane of the radiograph. In some embodiments, the projection can be derived directly from the registration and adjustment of the shape of the deformable 3D model as resulting from block 306 without the need for information regarding the source and projection plane of the radiograph. The 2D template on the modified radiograph or repositioned synthetic radiograph may be similarly projected based on a 3D template, or, since the modified radiograph or repositioned synthetic radiograph corresponds to a normalized view, may come from a 2D depiction of the implant that is stored in the library of implants.

In particular, in certain embodiments, image processing module 108 obtains a 3D template of an implant positioned with respect to the 3D model. Further, image processing module 108 generates a second 2D projection of the 3D template of the implant onto the projection plane in the one or more radiographs. Further, visualization module 112 displays the second 2D projection on the one or more radiographs on a display of the computing device.

In certain embodiments, the techniques presented herein determine a transformation between a 2D template in a normalized projection and an adapted representation of the implant in the projection of the original radiograph. The visualization module 112 may display both the original radiograph and a modified and/or repositioned synthetic radiograph side-by-side, or it may merely show the original radiograph, in which case the transformation can be computed and applied by image processing module 108 automatically (e.g., without notifying the user). When visualization module 112 shows more than one type of radiograph, the transformation or its inverse may be applied to propagate changes in position made by the user on one radiograph to the display of the other radiograph(s). This propagation can be performed in a synchronous (real-time) way or in an asynchronous (automatic update or update on demand) way, such as by image processing module 108.

In some embodiments, the techniques described here relate to 2D templating for hip replacement surgery. In that case, the adapted representation of the implant can, for example, relate to an adapted representation of the acetabular cup component to account for pelvic tilt, or to an adapted representation of the femoral component to account for an internal or external rotation of the leg.

In some embodiments, the techniques described here relate to 2D templating for knee replacement surgery. In that case, the adapted representation of the implant can, for example, relate to an adapted representation of the tibial or femoral component to account for flexion or internal or external rotation of the leg.

Certain embodiments of the disclosure also provide for systems and methods that allow the user to select certain anatomical parts to be shown or hidden. For example, visualization module 112 may take input from a user of a computing device and display or hide certain anatomical objects, parts, etc. For example, for 2D templating, the user is typically interested in one anatomical part at a time. Visual information from other anatomical parts may then distract the user or clutter the image. In some embodiments, one or more synthetic radiographs or modified radiographs may be computed as discussed herein based only on the virtual 3D model of the anatomical part of interest. In other embodiments, a modified radiograph may be generated in which all visual information not belonging to the anatomical part of interest is filtered out using image processing functions (e.g., performed by image processing module 108 and/or visualization module 112).

One advantage of such systems and methods is that the user may only be presented with the visual information that is relevant to the 2D templating process to be performed.

For example, in the case of hip surgery, the user might be mainly interested in 2D templating of the femoral component of a joint-replacement implant. In that case, the visual information of the pelvis might clutter the image. Certain embodiments of visualization module 112 may then produce and display one or more synthetic and/or modified radiographs showing only visual information of the femur.

In the case of knee surgery, the user might be mainly interested in 2D templating of the tibial component of a joint-replacement implant. In that case, the visual information of the femur might clutter the image. Certain embodiments of visualization module 112 may then produce and display one or more synthetic and/or modified radiographs showing only visual information of the tibia.

In the case of shoulder surgery, the user might be mainly interested in 2D templating of the humeral component of a joint-replacement implant. In that case, the visual information of the scapula might clutter the image. Certain embodiments of visualization module 112 may then produce and display one or more synthetic and/or modified radiographs showing only visual information of the humerus.

Another advantage is that such systems and methods may generate useful synthetic radiographs, such as repositioned synthetic radiographs, or modified radiographs that are not possible to generate in real life.

For example, in the case of hip surgery, a lateral radiograph is rarely considered useful, as the visual information of the left side of the acetabulum and femur overlay the visual information of the right side of the acetabulum and femur. It is almost impossible to discern which visual information belongs to which side of the anatomy. However, the systems and methods provided herein may produce a lateral synthetic radiograph or modified radiograph based solely on one hemipelvis and/or one femur. Such a synthetic radiograph or modified radiograph may present the anatomical parts as positioned in the original radiograph (e.g. rotated 90° with respect to a frontal radiograph), or the anatomical parts may be repositioned according to a normalized view as described in block 310.

For example, in the case of knee surgery, a lateral radiograph of the distal femur may be found confusing, as the visual information of the medial and lateral condyles are overlaid. The systems and methods provided herein, such as image processing module 108, may produce a synthetic radiograph based solely on the 3D model of the lateral or the medial condyle.

Certain embodiments herein further provide systems and methods that use one or more steps of generating one or more modified radiographs. For example, certain embodiments further provide systems and methods for 3D templating. 3D templating refers to selecting an appropriate (e.g., most appropriate) brand, type, shape, and/or size of implant, such as from a library of implants (e.g., stored as digital representations on a storage coupled to network 100), by comparing and overlaying a 3D model of the implant (meaning a digital representation of the implant in 3D) from a library of such 3D models on a 3D model of an anatomical object that is a digital representation of the anatomical object.

One drawback of surgical templating and planning on 3D models, is that, due to a lack of a visual reference, many users lose their bearings when viewing the 3D models. Many users, and clinicians in particular, therefore prefer 2D radiographs showing the anatomy in a normalized projection, even though much more information can be found in a 3D representation.

Some systems known in the art therefore display a visual reference together with the 3D models of the one or more anatomy parts of interest. This visual reference can be three or six lines or arrows representing the 3 axes of a coordinate system, a cube with letters on its faces, three intersecting planes, etc. However, such a visual reference may cause even more confusion if the 3D models of the anatomy parts of interest are not properly aligned with it.

Certain embodiments herein therefore provide systems and methods for improved 3D templating. In some embodiments, systems and methods are provided that generate 3D models of at least one anatomical object according to blocks 302 and 306 as described with respect to FIG. 3. Further, in some embodiments, one or more of these 3D models are repositioned according to blocks 304 and block 310 as described with respect to FIG. 3. In some such embodiments, a normalized projection comprises a definition of a desired position and orientation of the at least one anatomical object relative to a common coordinate system. The position and orientation of the at least one anatomical object within the common coordinate system can be defined in terms of its anatomical coordinate system.

In some embodiments, visualization module 112 displays the 3D models of the anatomy parts of interest. For example, visualization module 112 displays the positioned 3D model with respect to the projection plane on a display of the computing device. Depending on the type of statistical data in the deformable 3D model, the 3D models may contain surface data and/or grey-value data (e.g., volumetric data), and they may be displayed by surface rendering and/or volume rendering respectively. In some embodiments, visualization module 112 displays a visual reference indicating the common coordinate system together with the 3D models.

In certain embodiments, one approach to presenting 3D information in a way that looks more familiar to the user, is to produce synthetic stacked medical images and to present those to the user in the same way as CT or MM images are typically shown. In some embodiments, visualization module 112 displays 2D slices of the positioned 3D model (e.g., corresponding to synthetic stacked medical images).

In certain embodiments, image processing module 108 generates such 2D slices by performing blocks 302 and 306 of FIG. 3 to create a 3D model based on a deformable 3D model of an anatomical object in a radiograph. In some embodiments, the deformable 3D model contains grey-value information (e.g., appearance model, active appearance model, intensity model, and/or active shape model) assigned to the nodes of one or more volume meshes. In some embodiments, the deformable 3D model comprises a volume mesh for each anatomical object and/or the 3D model comprises at least one virtual 3D model for each anatomical object.

The image processing module 108 then obtains a definition of a normalized pose of the at least one anatomical object (e.g., a desired position and orientation) and repositions each of the volume meshes and/or 3D models according to the definition of the normalized pose. In certain embodiments, the normalized pose is defined in terms of a position and orientation of each of the at least one anatomical object with respect to a common coordinate system. The position and orientation of an anatomical object can be defined by means of its anatomical coordinate system.

In some embodiments, the 3D model is displayed by visualization module 112 by means of one or more 2D images (e.g., generated by image processing module 108 according to techniques discussed herein) representing slices through the 3D model. In certain embodiments, the slices are made perpendicular to one or more of the axes of the common coordinate system. In certain embodiments, a slice is generated by cutting through the 3D model along a plane, and generating a 2D image comprising pixels. In certain embodiments, the color of each pixel is determined by interpolating between the grey values of the nodes of the one or more volume meshes of the 3D model. Different interpolation methods may be utilized (e.g. nearest-neighbor interpolation, linear interpolation, polynomial interpolation, etc.). The slices may be generated, such as by image processing module 108, as they are displayed by visualization module 112, or alternatively they may be generated once and stored, such as in image data storage 106. Alternatively, a voxel mesh (e.g., pixel mesh) may be computed (e.g., by image processing module 108) wherein the color of each voxel (e.g., pixel) may be determined by interpolating between the grey values of the nodes of the one or more volume meshes of the instance of the deformable 3D model. 2D images may then be generated (e.g., by image processing module 108) by retrieving one layer of voxels from the voxel mesh.

In certain embodiments, the colors of the pixels and/or voxels may be further determined by applying one or more filters or image-processing operations before and/or after the interpolation, such as by image processing module 108. For example, if the deformable 3D model comprises more than one volume mesh, the grey values of each of these volume meshes may be adjusted to different hues. This may, for example, result in synthetic stacked medical images in which different anatomy parts of interest are color coded.

In some embodiments, the 2D images represent coronal, axial and/or sagittal slices through the anatomy. The visualization module 112 may display one or more these at the same time, optionally in combination with a 3D view of the 3D model. Some embodiments of visualization module 112 may present the user with an interactive way to scroll through the slices.

The methods and systems provided herein may allow the user to perform measurements in three dimensions and/or to perform 3D templating as discussed. In that case the user is able to select the brand, type, shape and/or size of implant that best fits the anatomy of the patient by overlaying 3D models of the implants from an implant library on the displayed images of the anatomy. The 3D model of an implant can then be sliced (e.g., by image processing module 108) by the plane of an image and represented by its cross section in that plane (e.g. by displaying the cross section's contour onto the image, or by overlaying the 2D shape of the cross section in an opaque or partly transparent color into the image).

Certain embodiments of the present disclosure provide systems and methods, such as measurement and analysis module 110, that allow the user to perform measurements on anatomy in a more accurate way. This also offers the possibility to repeatedly perform the same measurements in a reliable way.

Certain embodiments of the present disclosure therefore also provide systems and methods, such as measurement and analysis module 110, for making and comparing measurements at different stages before, during and/or after a medical intervention. For example, the techniques described herein can be performed based on 2D radiographs taken before, during, or after a medical intervention, and can therefore be used in systems for pre-operative planning and templating, systems for intra-operative verification or navigation and post-operative evaluation. All of these can be made to take one or more 2D radiographs as input and facilitate repeatable and reliable measurements.

In some embodiments, measurement and analysis module 110 is configured to define measurements based on anatomical landmarks, such as those discussed herein. For example, a linear measurement can have two anatomical landmark points as its end points. For example, a diameter measurement can have a substantially circular or spherical anatomical landmark as its input. For example, an angular measurement can be defined using three anatomical landmark points. For example, image processing module 108 may perform blocks 302 and 304 to generate a 3D model of at least one anatomical object from a radiograph. Image processing module 108 can further define one or more landmarks and/or an anatomical coordinate system associated with the at least one anatomical object in the 3D model, such as discussed with respect to block 310. In some embodiments, systems for pre-operative planning or templating, intra-operative verification or navigation and post-operative evaluation may use such resulting landmarks for the definition of measurements. Alternatively, systems can use landmarks identified on modified or synthetic radiographs. When the same landmarks are generated before, during, and after the medical intervention, the same measurements can be performed and compared at these different stages, such as by a user of or automatically by measurement and analysis module 110.

For example, in certain embodiments, image processing module 108 can define one or more anatomical landmarks associated with the at least one anatomical object in the 3D model. Further, measurement and analysis module 110 can perform one or more measurements of the at least one anatomical object in the 3D model based on the one or more anatomical landmarks. Image processing module 108 can identify the one or more landmarks in one or more additional radiographs. Measurement and analysis module 110 can perform one or more additional measurements of the at least one anatomical object in the one or more additional radiographs based on the one or more anatomical landmarks.

Figure 16:
FIG. 16 illustrates a modified AP pelvic radiograph with a measurement of a lateral center edge angle.

For example, if the medical intervention is a corrective surgery for femoroacetabular impingement, the user may pre-operatively measure the lateral center edge angle on a modified AP pelvic radiograph as the angle between a vertical line and a line connecting the center of the femoral head and the lateral edge of the acetabulum, such as shown in FIG. 16. To this end, the femoral head and the edge of the acetabulum may be defined as landmarks. This measurement, its definition and the landmarks that its definition is based on may then be stored, such as in storage 106. Intra-operatively, the same landmarks may be identified on a modified intra-operative radiograph, and a measurement according to the same definition may be made and compared to the pre-operative value, or used to guide the reshaping of the acetabulum by comparing it to a pre-operatively planned target value. Post-operatively, the same landmarks may be identified on a modified post-operative radiograph, and a measurement according to the same definition may be made and compared to the pre-operative value or to a pre-operatively planned target value.

It should be noted that in certain embodiments, one or more of the methods described herein is a computer-implemented method. Further, certain steps may be performed automatically, manually by a user of a computing device, or partially manually and partially automatically such as based on input from a user of a computing device.

Further, in certain embodiments, a person, such as a clinician, engineer, technician, medical professional, etc., may use a computing device to, or the computing device itself may automatically perform one or more steps of one or more methods described herein.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims. Further, one or more blocks/steps may be removed or added.

Various embodiments disclosed herein provide for the use of a computer system to perform certain features. A skilled artisan will readily appreciate that these embodiments may be implemented using numerous different types of computing devices, including both general-purpose and/or special-purpose computing system environments or configurations. Examples of well-known computing systems, environments, and/or configurations that may be suitable for use in connection with the embodiments set forth above may include, but are not limited to, personal computers, server computers, hand-held or laptop devices, multiprocessor systems, microprocessor-based systems, programmable consumer electronics, network PCs, minicomputers, mainframe computers, distributed computing environments that include any of the above systems or devices, and the like. These devices may include stored instructions, which, when executed by a microprocessor in the computing device, cause the computer device to perform specified actions to carry out the instructions. As used herein, instructions refer to computer-implemented steps for processing information in the system. Instructions can be implemented in software, firmware or hardware and include any type of programmed step undertaken by components of the system.

A microprocessor may be any conventional general-purpose single- or multi-chip microprocessor such as a Pentium® processor, a Pentium® Pro processor, a 8051 processor, a MIPS® processor, a Power PC® processor, or an Alpha® processor. In addition, the microprocessor may be any conventional special-purpose microprocessor such as a digital signal processor or a graphics processor. The microprocessor typically has conventional address lines, conventional data lines, and one or more conventional control lines.

Aspects and embodiments of the inventions disclosed herein may be implemented as a method, apparatus or article of manufacture using standard programming or engineering techniques to produce software, firmware, hardware, or any combination thereof. The term "article of manufacture" as used herein refers to code or logic implemented in hardware or non-transitory computer readable media such as optical storage devices, and volatile or non-volatile memory devices or transitory computer readable media such as signals, carrier waves, etc. Such hardware may include, but is not limited to, field programmable gate arrays (FPGAs), application-specific integrated circuits (ASICs), complex programmable logic devices (CPLDs), programmable logic arrays (PLAs), microprocessors, or other similar processing devices.

What is claimed is:
1. A computer-implemented method of generating a computer-based radiographic representation of at least part of one anatomical object, the method comprising:
  obtaining, at a computing device, one or more radiographs of at least part of one anatomical object, each of the one or more radiographs comprising a 2D visual represen- tation of the at least part of one anatomical object in a corresponding projection plane;

obtaining, by the computing device, information indicative of a normalized projection comprising information indicative of a desired position and orientation of the at least part of one anatomical object with respect to a first projection plane of the one or more corresponding projection planes, wherein the desired position and orientation of the at least part of one anatomical object with respect to the first projection plane is different than an actual position and orientation of the at least part of one anatomical object in the one or more radiographs;

generating, by the computing device, a 3D model of the at least part of one anatomical object based on the one or more radiographs;

repositioning, by the computing device, the 3D model based on the information indicative of the normalized projection;

generating, by the computing device, a 2D projection of the repositioned 3D model onto the first projection plane, the generating the 2D projection comprising:
tracing rays from at least one position of at least one source of x-rays used to generate one or more of the one or more radiographs through one or more pixels of the first projection plane, wherein the at least one position is with respect to the first projection plane; and
for each of the one or more pixels, determining a grey value for the pixel based on a length of a ray associated with the pixel that is included within the 3D model; and modifying, by the computing device, at least one of the one or more radiographs of the at least part of one anatomical object to conform to the 2D projection.

2. The method of claim 1, wherein the one or more of the one or more radiographs further comprise position information of the at least one position.

3. The method of claim 1, wherein generating the 3D model comprises adjusting a shape of the 3D model to align with a shape of the at least part of one anatomical object in the one or more radiographs.

4. The method of claim 1, wherein the 3D model includes statistical information about the at least part of one anatomical object, the statistical information based on a plurality of different instances of the at least part of one anatomical object and comprising one or more of a statistical shape model, an articulated statistical shape model, an active shape model, an appearance model, and an intensity model.

5. The method of claim 1, wherein the tracing comprises:
tracing rays from the at least one position along points of the 3D model where the 3D model is tangential to the traced rays, wherein the 2D projection comprises a contour line representation.

6. The method of claim 1, wherein for each of the one or more pixels, the grey value of the pixel is further based on a variable attenuation factor.

7. The method of claim 1, wherein modifying the at least one of the one or more radiographs comprises:
identifying one or more projected contours of the at least part of one anatomical object in the 2D projection; and
morphing the at least one of the one or more radiographs to align one or more contours of the at least part of one anatomical object in the at least one of the one or more radiographs to the one or more projected contours.

8. The method of claim 1, wherein modifying the at least one of the one or more radiographs comprises performing non-rigid image registration techniques to register the at least one of the one or more radiographs to the 2D projection.

9. The method of claim 1, further comprising:
displaying the at least one modified radiograph on a display of the computing device for visualization of the at least part of one anatomical object from the desired position and orientation.

10. The method of claim 9, further comprising:
defining one or more anatomical landmarks associated with the at least part of one anatomical object in the 3D model;
performing one or more measurements of the at least part of one anatomical object in the 3D model based on the one or more anatomical landmarks; and
displaying the one or more measurements on the display.

11. The method of claim 9, further comprising:
defining one or more anatomical landmarks associated with the at least part of one anatomical object in the 3D model, wherein displaying the at least one modified radiograph comprises displaying information indicative of the one or more anatomical landmarks.

12. The method of claim 9, further comprising:
displaying a 2D template of an implant on the display in an orientation and position relative to the position and orientation of the at least part of one anatomical object in the at least one modified radiograph.

13. The method of claim 1, wherein modifying the at least one of the one or more radiographs of the at least part of one anatomical object based on the 2D projection comprises applying a transformation to the at least one of the one or more radiographs to align the at least one of the one or more radiographs with the 2D projection, and further comprising:
applying an inverse of the transformation to a 2D template of an implant; and
displaying the transformed 2D template of the implant along with the at least one of the one or more radiographs on a display of the computing device.

14. The method of claim 1, wherein repositioning the 3D model comprises applying a transformation to the 3D model to align with the desired position and orientation of the at least part of one anatomical object with respect to the first projection plane, and further comprising:
applying an inverse of the transformation to a 2D template of an implant as positioned with respect to the at least one modified radiograph to generate a 3D template of the implant positioned with respect to the 3D model;
generating, by the computing device, a second 2D projection of the 3D template of the implant onto the corresponding projection plane in another one or more of the one or more radiographs; and
displaying the second 2D projection on the another one or more of the one or more radiographs on a display of the computing device.

15. The method of claim 1, further comprising:
obtaining a 3D template of an implant positioned with respect to the 3D model;
generating, by the computing device, a second 2D projection of the 3D template of the implant onto the corresponding projection plane in another one or more of the one or more radiographs; and
displaying the second 2D projection on the another one or more of the one or more radiographs on a display of the computing device.

16. The method of claim 1, further comprising displaying the repositioned 3D model with respect to the first projection plane on a display of the computing device.

17. The method of claim 16, further comprising displaying 2D slices of the repositioned 3D model.

18. The method of claim 1, further comprising:
defining one or more anatomical landmarks associated with the at least part of one anatomical object in the 3D model;
performing one or more measurements of the at least part of one anatomical object in the 3D model based on the one or more anatomical landmarks;
identifying the one or more anatomical landmarks in one or more additional radiographs; and
performing one or more additional measurements of the at least part of one anatomical object in the one or more additional radiographs based on the one or more anatomical landmarks.

19. The method of claim 1, further comprising:
determining based on the 3D model an optimal projection plane, wherein the repositioning is performed with respect to the optimal projection plane, and the first projection plane comprises the optimal project plane.

20. A non-transitory computer-readable medium having computer-executable instructions stored thereon, which, when executed by a processor of a computing device, cause the computing device to perform a method of generating a computer-based radiographic representation of at least part of one anatomical object, the method comprising:
obtaining, at the computing device, one or more radiographs of at least part of one anatomical object, each of the one or more radiographs comprising a 2D visual representation of the at least part of one anatomical object in a corresponding projection plane;
obtaining, by the computing device, information indicative of a normalized projection comprising information indicative of a desired position and orientation of the at least part of one anatomical object with respect to a first projection plane of the one or more corresponding projection planes, wherein the desired position and orientation of the at least part of one anatomical object with respect to the first projection plane is different than an actual position and orientation of the at least part of one anatomical object in the one or more radiographs;
generating, by the computing device, a 3D model of the at least part of one anatomical object based on the one or more radiographs;
repositioning, by the computing device, the 3D model based on the information indicative of the normalized projection;
generating, by the computing device, a 2D projection of the repositioned 3D model onto the first projection plane, the generating the 2D projection comprising:
tracing rays from at least one position of at least one source of x-rays used to generate one or more of the one or more radiographs through one or more pixels of the first projection plane, wherein the at least one position is with respect to the first projection plane; and
for each of the one or more pixels, determining a grey value for the pixel based on a length of a ray associated with the pixel that is included within the 3D model; and
modifying, by the computing device, at least one of the one or more radiographs of the at least part of one anatomical object to conform to the 2D projection.

21. A computing device comprising:
a memory; and
a processor configured to:
obtain one or more radiographs of at least part of one anatomical object, each of the one or more radiographs comprising a 2D visual representation of the at least part of one anatomical object in a corresponding projection plane;
obtain information indicative of a normalized projection comprising information indicative of a desired position and orientation of the at least part of one anatomical object with respect to a first projection plane of the one or more corresponding projection planes, wherein the desired position and orientation of the at least part of one anatomical object with respect to the first projection plane is different than an actual position and orientation of the at least part of one anatomical object in the one or more radiographs;
generate a 3D model of the at least part of one anatomical object based on the one or more radiographs;
reposition the 3D model based on the information indicative of the normalized projection;
generate a 2D projection of the repositioned 3D model onto the first projection plane, the generating the 2D projection comprising:
tracing rays from at least one position of at least one source of x-rays used to generate one or more of the one or more radiographs through one or more pixels of the first projection plane, wherein the at least one position is with respect to the first projection plane; and
for each of the one or more pixels, determining a grey value for the pixel based on a length of a ray associated with the pixel that is included within the 3D model; and
modify at least one of the one or more radiographs of the at least part of one anatomical object to conform to the 2D projection.

* * * * *